United States Patent [19]

Gates

[11] Patent Number: 4,836,198
[45] Date of Patent: Jun. 6, 1989

[54] PORTABLE VENTILATING DEVICE

[75] Inventor: William M. Gates, Atchison, Kans.

[73] Assignee: Stein-Gates Medical Equipment, Inc., Atchison, Kans.

[21] Appl. No.: 78,162

[22] Filed: Jul. 27, 1987

[51] Int. Cl.[4] .......................... A62B 7/00; F04B 17/00
[52] U.S. Cl. ............................ 128/205.18; 128/205.24; 417/404; 417/349
[58] Field of Search .................... 128/205.18, 204.21, 128/204.18, 205.24; 417/403, 404, 349, 505

[56] References Cited

U.S. PATENT DOCUMENTS

| | | | |
|---|---|---|---|
| Re. 24,193 | 10/1947 | Emerson | 128/29 |
| 2,770,231 | 11/1956 | Falk | 128/29 |
| 3,225,758 | 12/1965 | Morch | 128/29 |
| 3,530,872 | 9/1970 | Arp | 417/404 |
| 3,530,873 | 9/1970 | Arp | 417/404 |
| 4,076,021 | 2/1978 | Thompson | 128/145.6 |
| 4,141,355 | 2/1979 | Apple | 128/145.6 |
| 4,163,911 | 8/1979 | Simes et al. | 128/205.18 |
| 4,215,681 | 8/1980 | Zalkin et al. | 128/204.21 |
| 4,243,029 | 1/1981 | Apple | 128/204.21 |
| 4,384,576 | 5/1983 | Farmer | 128/205.18 |
| 4,472,082 | 9/1984 | Kroling | 405/186 |
| 4,493,614 | 1/1985 | Chu et al. | 417/22 |
| 4,587,967 | 5/1986 | Chu et al. | 128/204.21 |

Primary Examiner—A. Michael Chambers

[57] ABSTRACT

A portable ventilating device for ventilating patients in the field. A reciprocating piston divides a cylinder into a pressure chamber and a spring chamber in which a compression spring acts against the piston. Gas pressure applied to the pressure chamber opposes the spring force and reciprocates the piston. As the piston reciprocates ventilating gas is forced out of the piston chamber through a ventilation line equipped with a check valve. Alternative embodiments provide gas pressure assistance to the spring, make use of the gas which powers the device as the ventilating gas, and provide adjustment of the duration for the time periods gas is applied to the cylinder.

14 Claims, 2 Drawing Sheets

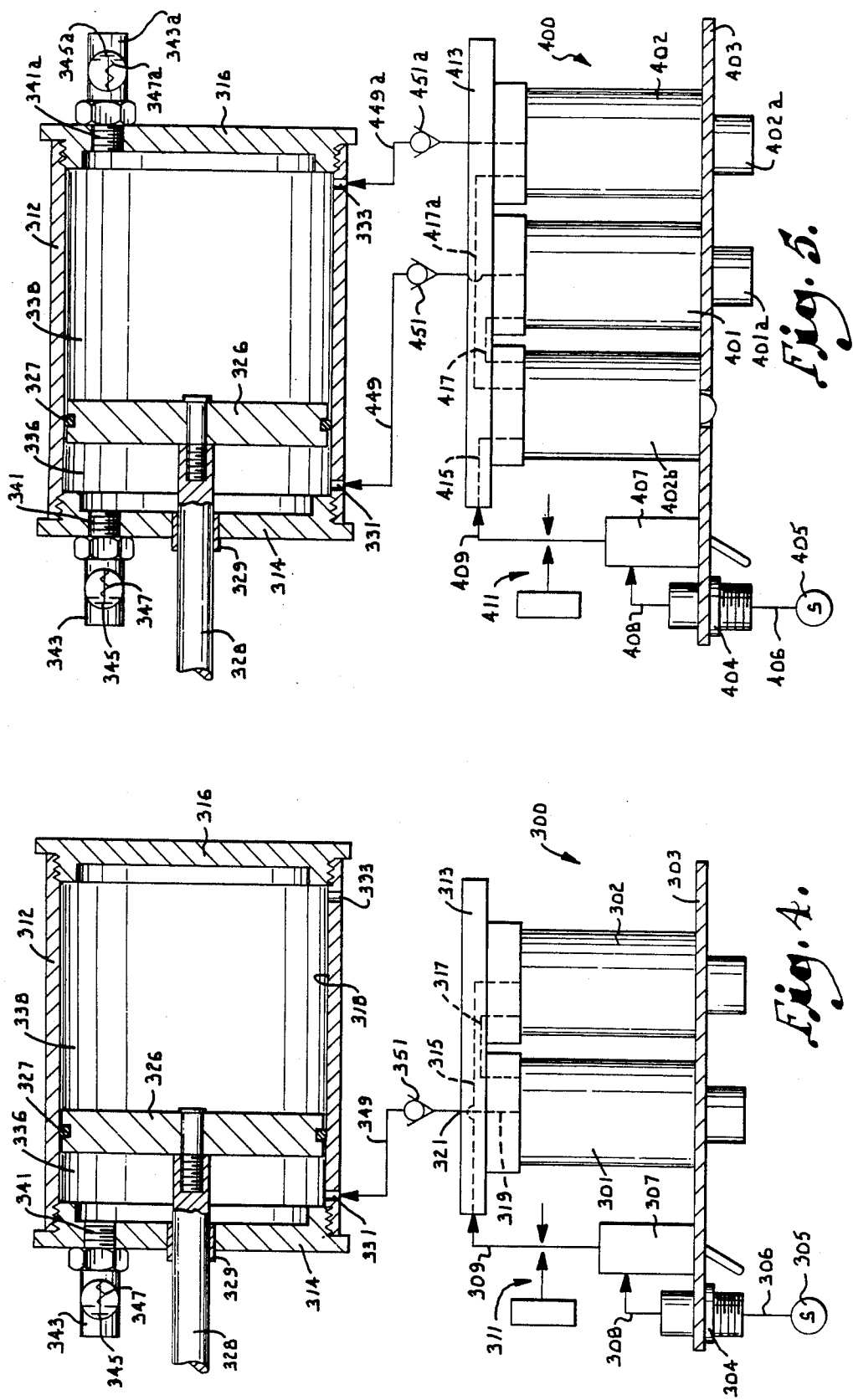

PORTABLE VENTILATING DEVICE

BACKGROUND AND SUMMARY OF THE INVENTION

This invention relates in general to the ventilation of injured or ill persons and deals more particularly with a portable ventilating device which is well suited for use in the field.

In the event of certain medical emergencies, it is necessary for injured or ill persons to be artificially ventilated in order to prevent death and other serious consequences. For example, it is necessary for the armed forces to be capable of ventilating injured personnel in the field or persons who have been subjected to smoke inhalation or poisonous gases. In the past, the portable field ventilators that have been available have not been as light as desirable, have not been easy to use and service in the field, and have not been useful in the absence of operating power. In addition, the provision of a portable ventilating device capable of ventilating at a constant rate and volume without undue complexity has not been accomplished.

The present invention is directed to an improved ventilating device which is constructed in a unique manner to overcome the aforementioned problems. Among the objects of the invention are to provide a ventilating device which is light in weight, easy to use, easy to assemble, disassemble and maintain, easily decontaminated, easy to store, capable of manual operation when operating power is unavailable, and constructed of parts which are not subject to degradation even after the device has been stored and/or used over a prolonged period.

DETAILED DESCRIPTION OF THE INVENTION

In the accompanying drawings which form a part of the specification and are to be read in conjunction therewith and in which like reference numerals are used to indicate like parts in the various views:

FIG. 4 is a longitudinal sectional view of a ventilating device constructed according to yet another embodiment of the invention; and FIG. 5 is a longitudinal sectional view of a ventilating device constructed according to a further embodiment of the invention.

Figure 1:
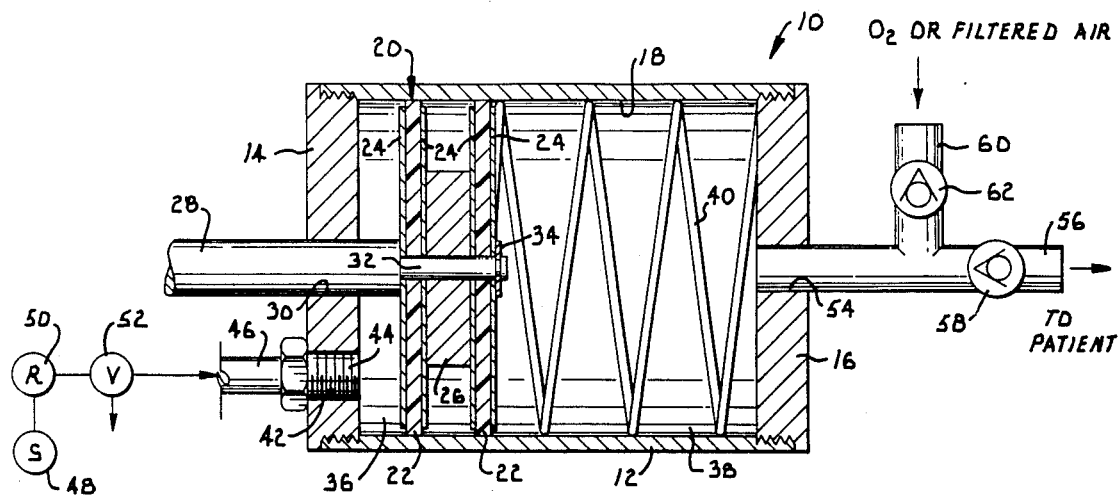
FIG. 1 is a longitudinal sectional view of a ventilating device constructed according to one embodiment of the present invention.

Referring now to the drawing in more detail and initially to FIG. 1, numeral 10 generally designates a portable ventilating device which is suitable for use in the field by the armed forces and others. The ventilating device 10 includes a hollow cylinder 12 which may be constructed of aluminum suitable material. The opposite ends of cylinder 12 are covered by aluminum end plates 14 and 16. Preferably, the opposite ends of cylinder 12 are internally threaded in order to mate with external threads on the end plates 14 and 16. The end plates can be suitably sealed to the cylinder 12.

A piston chamber 18 is formed within cylinder 12 in order to receive a reciprocating piston which is generally identified by numeral 20. The piston 20 is formed by a pair of spaced apart disks 22 which seal at their edges against the inside surface of cylinder 12. Each disk 22 is sandwiched between a pair of retainer plates 24. The disks 22 are separated from one another by a spacer 26. An elongated handle 28 extends from piston 20 and closely through a circular opening 30 which is formed centrally in plate 14. The end of handle 28 carries a small stud 32 which extends centrally through the disks 22, the retainer plates 24 and the spacer 26. A fastener 34 is secured on the end of stud 32 in order to secure the parts of piston 20 together. The handle 28 extends externally of cylinder 12 and is thus available for manual operation of the ventilating device in the event of an absence of operating power.

Piston 20 separates the piston chamber 18 into a pressure chamber 36 located on the left side of the piston and a spring chamber 38 located on the right side of the piston. A large compression spring 40 is fitted in the spring chamber 38 and acts at its opposite ends against the piston 20 and the end plate 16. The compression spring 40 thus exerts a force on piston 20 which continuously urges the piston to the left as viewed in FIG. 1. It is noted that the force exerted on the piston by spring 40 increases as the spring is progressively compressed due to movement of piston 20 to the right.

The force exerted on piston 20 by spring 40 is opposed by pneumatic pressure which is applied to the pressure chamber 36. A pressure port 42 is formed through plate 14 and receives a threaded fitting 44. A flexible hose 46 connects with fitting 44 and forms a high pressure line which receives compressed air or compressed oxygen from a suitable source 48 which may be conventional tank containing gas under pressure. A pressure regulator 50 regulates the pressure of the gas which is applied to hose 46. The hose is also equipped with a valve 52 which can be opened to open the hose and close to vent the hose and thus relieve the pressure within the pressure chamber 36.

A ventilating port 54 is formed through the opposite end plate 16. A ventilating line 56 extends from the ventilating port 54 and may be applied to a patient in order to provide ventilating gas to the patient. A check valve 58 in line 56 allows flow through line 56 away from the piston chamber 18 but not toward the piston chamber. A supply line 60 has a tee connection with the ventilating line 56 and is equipped with a check valve 62 which allows flow through line 60 toward chamber 18 but not away from the chamber. The supply line 60 may connect with an oxygen tank or other source of oxygen or may simply be connected with a source of filtered air.

The ventilating device 10 is small enough to be easily carried in the field by medics or other medical personnel. When compressed air or another gas under pressure is connected with the fitting 44 through hose 46, the gas pressure is applied through the hose to the pressure chamber 36. The force applied to piston 20 by the gas pressure is able to overcome the force of the compression spring 40, and this moves the piston to the right as viewed in FIG. 1. Movement of the piston to the right in turn causes the oxygen or air in the spring chamber 38 to be forced through the ventilating line 56 and valve 58 to the patient, where it can be used for ventilating purposes. It is noted that the check valve 62 prevents the ventilating gas from flowing through the supply line 60 during movement of the piston to the right.

As piston 20 moves to the right, spring 40 is progressively compressed and eventually exerts a force on the piston which is greater than the force exerted by the gas pressure in chamber 36. This occurs when piston 20 approaches end plate 16. Then, spring 40 begins to move the piston 20 to the left, and valve 52 is closed to disconnect the source 48 from chamber 36 and at the same time relieve the pressure in the pressure chamber. Consequently, spring 40 moves piston 20 to the left until the piston approaches the opposite end plate 14, as shown in FIG. 1. At this time, spring 40 is decompressed, and valve 52 is again opened to apply gas pressure for driving piston 20 to the right. During movement of piston 20 to the left, oxygen or air is drawn through he supply line 60 and valve 62 into the spring chamber 38, and the air or oxygen is thereafter ejected to the patient through line 56 during the next rightward stroke of the piston.

In this manner, the ventilating device 10 is powered and controlled pneumatically by the portable source 48. Piston 20 reciprocates in cylinder 12 at a constant rate, thus providing a constant volume of air or oxygen during each stroke. The ventilation that is provided to the patient is thus both constant volume and constant rate for effective ventilation.

In the event that the source 48 is depleted or otherwise malfunctions, the ventilating device 10 can be manually powered simply by grasping handle 28 and extending it into the cylinder 12. At the end of the rightward stroke of piston 20, the handle is released so that spring 40 can return piston 20 to the left. The provision of handle 28 and its ability to permit manual operation in the absence of operating power is an important feature of the invention which enhances the versatility of the ventilating device 10.

Figure 2:
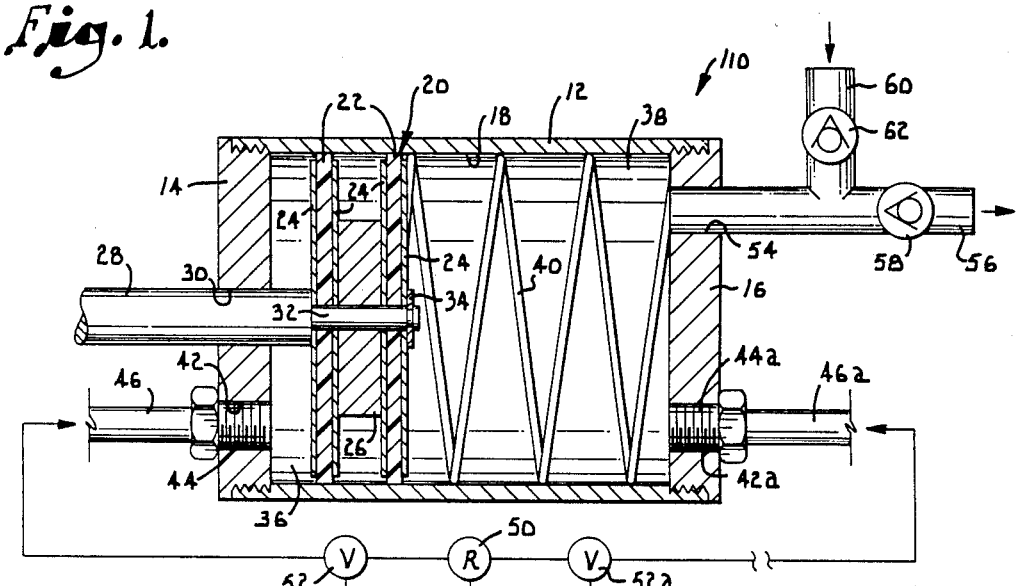
FIG. 2 is a longitudinal sectional view of a ventilating device constructed according to another embodiment of the invention.

Referring now to FIG. 2, numeral 110 generally identifies an alternative embodiment of the ventilating device which is constructed for the most part in the same manner as the ventilating device 10 shown in FIG. 1. The same reference numerals are employed in FIGS. 1 and 2 to identify parts which are substantially the same in the two embodiments. The principal difference in the FIG. 2 embodiment is that hose 46 forms only one of two branches of the high pressure line which connects with the pressure source 48 through regulator 50. The second branch of the high pressure line includes a hose 46a which is equipped with a valve 52a and which connects with a fitting 44a. The fitting 44a is in turn threaded through a port 42a formed in end plate 16.

The operation of ventilating device 110 is identical to that of ventilating device 10 with one exception. When the piston 20 has reached its limiting position to the right, valve 52a is opened to connect the pressure source 48 with the spring chamber 38 through hose 46a and fitting 44a. Thus, gas pressure from source 48 is applied to the spring chamber 38 and assists the compressed spring 40 in moving piston 20 to the right during its return stroke. At the end of the return stroke, valve 52a is closed to relieve the pressure in the spring chamber 38 at the same time as valve 52 is opened to again apply gas pressure to the pressure chamber 36.

The assistance that is provided by the gas pressure in effecting the return stroke of piston 20 facilitates efficient operation of the device. It is noted that the gas which is applied under pressure from the source 48 should in this case be the same as the gas which is supplied to the spring chamber 38 through the supply line 60. Air is preferred in most cases, although oxygen or oxygen enriched air can be used.

Figure 3:
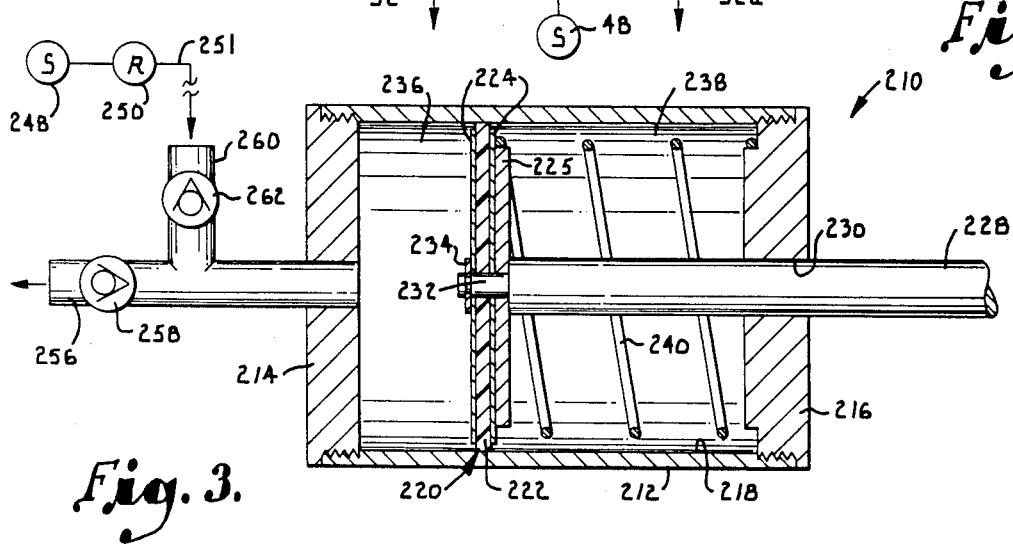
FIG. 3 is a longitudinal sectional view of a ventilating device constructed according to a third embodiment of the invention.

Referring now to FIG. 3, numeral 210 generally designates a third embodiment of the ventilating device. In some respects, the ventilating device 210 is similar to devices 10 and 110. An aluminum cylinder 212 is enclosed at its opposite ends by end plates 214 and 216 and defines a pisston chamber 218 in which a piston 220 is mounted for reciprocation. The piston includes a single disk 222 which seals at its periphery against the inside surface of cylinder 218. Disk 222 is sandwiched between a pair of retainer plates 224. A backing plate 225 is held against one of the retainer plates 224. A elongated handle 228 extends from piston 220 through an opening 230 in the center of the right end plate 216 and is accessible from the exterior of the cylinder in order to effect manual operation of the ventilating device 210. The parts of piston 220 are held together by a stud 232 which extends from the end of handle 228 through the center of the piston assembly and which receives a suitable fastener 234. As in the other embodiments, the spring chamber 238 receives a compression spring 240, and a pressure chamber 236 is formed on the opposite side of the piston from the spring chamber.

In the FIG. 3 embodiment, the ventilating port 254 extends through end plate 14 and connects with a ventilating line 256 which is equipped with a check valve 258. The supply line 260 is equipped with a check valve 262 and has a tee connection with line 256. In the arrangement shown in FIG. 3, the supply line 260 serves both to supply the ventilating device with the ventilating gas and to form the pressure line which applies the gas pressure used to move piston 220 against the spring force. A source 248 of compressed air or compressed oxygen connects through a pressure regulator 250 with a flexible pressure line 251 which leads to connection with the supply line 260.

In operation of the ventilating device 210, compressed air or oxygen flows from source 248 through hose 251 and line 260 into chamber 236 where it applies a force to piston 220 opposing the force of spring 240. Piston 220 is thus moved to the right and progressively compresses spring 240 during such movement. Chamber 238 may be vented, although it need not be and it not, the air in it is compressed as the piston moves to the right. At the end of the rightward stroke of the piston, spring 240 is compressed sufficiently to overcome the force of the gas pressure, and spring then returns piston 220 to the left or toward the ventilating port 254. During movement of piston 222 a left, the air or oxygen in pressure chamber 236 is ejected through valve 258 and the ventilating line 256 to the patient. At the end of the leftward stroke of the piston, spring 240 is decompressed and the pressure which is applied to chamber 36 is able to overcome the spring force and again force the piston to the right.

Again, oxygen or air for ventilation of the patient is provided at a constant rate and a constant volume. The major operational difference in the embodiment shown in FIG. 3 is that the decompressed gas (air or oxygen) which is used to power the device is also supplied to the patient as the ventilating gas. Consequently, gas is conserved and there is no need to provide separate pressure and supply lines as in the other embodiments.

FIG. 4 depicts a pneumatic valve arrangement which is generally designated by reference numeral 300 and which can be used either by itself to ventilate patients or in combination with a cylinder 312. The valve system 300 includes a pair of pneumatic valves 301 and 302 mounted side by side on a mounting plate 303. An inlet port 304 is also mounted on plate 303 and may be connected with a source 305 of compressed air (or other gas) by a pneumatic line 306. The inlet port 304 connects with an on-off switch 307 through line 308. When switch 307 is in the "on" position, line 308 connects through it with another line 309 equipped with an adjustable flow restrictor 311. In the "off" position, switch 307 blocks flow between lines 308 and 309 and thus deactivates the device 300.

Line 309 connects through the flow restrictor 311 with a block 313 which is specially ported. The porting of block 313 is such that incoming gas is directed through passage 315 to valve 302 and, when valve 302 is open, from valve 302 to valve 301 via passage 317. When valve 301 is open, it supplies gas to another passage 319 which terminates in an outlet port 321.

Valves 301 and 302 are pneumatic timers which are open for adjustable time periods that may be varied in accordance with the settings of respective adjustment dials 301a and 302a. Valve 301 is open for a time period (inspiratory time) which depends on the setting of knob 301a and closes when the inspiratory time period has elapsed. Similarly, valve 302 is open for a time period (expiratory time) that may be varied by adjusting knob 302a. The timer valves 301 and 302 thus cycle open and closed during alternate inspiratory times and expiratory times that may be adjusted independently. During the inspiratory time, valve 301 is open to provide compressed gas flow through the outlet port 321 from the holding tank associated with valve 301. At the end of the inspiratory time, valve 301 closes to terminate flow through port 321. Valve 302 then opens to permit gas flow to valve 3091 during the expiratory time. When the expiratory time has elapsed, valve 302 closes and valve 301 opens to allow the gas that has accummulated in the associated accumulator to discharge through port 321 during the next inspiratory time period.

The valve arrangement 300 can be used by itself to supply air or other gas directly to the patient. In this case, a supply line from outlet port 321 to the patient supplies air during the inspiratory periods and closes during expiratory periods.

The valve arrangement can also be used with a cylinder 312 having a piston 326 which reciprocates in a bore 318 in the cylinder. A pressure chamber 336 is presented on the left side of the piston and another chamber 338 is presented on its right side. The cylinder 312 is closed at its opposite ends by threaded end caps 314 and 316. Piston 316 is sealed to cylinder 312 by an O-ring 327 and is equipped with a handle 328 which extends from the piston through a bushing 328 fitted in the end cap 314. Cylinder 312 has an inlet port 331 near its left end in communication with chamber 336 and a vent port 333 near its right end in communication with chamber 338.

Cap 314 has an outlet port 341 which connects with a supply line 343 leading to the patient. A one way valve 345 is provided in line 343 and allows flow only in a direction from the cylinder toward the patient. Valve 345 is urged by a compression spring 347 toward its closed position but can be forced open when the gas pressure in chamber 336 is high enough to overcome the spring force. A gas line 349 equipped with a check valve 351 extends from port 321 to port 331.

In operation, compressed gas is supplied during the inspiratory period to the outlet port 321 and through line 349 to the pressure chamber 336 via port 331. The pressure in chamber 336 forces piston 326 to the right, with the air in chamber 338 being vented through the vent port 333. At the end of the inspiratory period, piston 326 is moved to the left by pulling on handle 328 (or by spring force or fluid pressure), and this forces the gas in chamber 336 out through valve 345 to line 343 and the patient. At the end of the travel of piston 326 to the left, the inspiratory time again occurs and the piston is driven to the right. In this manner, the piston is cycled back and forth to ventilate the patient. It should be noted that the valve arrangement 300 can be used to power the ventilator 10 shown in FIG. 1.

FIG. 5 depicts another embodiment of the invention which includes a pneumatic valve arrangement 400 which is in large part similar to the valve arrangement 300 described previously. A pair of valves 401 and 402 along with a third valve 402b are mounted on a plate 403 having an inlet 404 which receives compressed gas from a source 405 via line 406. An on-off switch 407 controls flow between lines 408 and 409, the latter of which s equipped with a flow restrictor 411. Line 409 connects with a block 413 which is ported to supply incoming gas to valve 402b along passage 415 and from valve 402b to valves 401 and 402 via passages 417 and 417a, respectively. Valve 401 connects with one outlet port 421 via passages 419, while valve 402 connects with another outlet port 421a via passage 419a.

Valves 401 and 402 are opened during alternating inspiratory and expiratory times which can be varied by adjustment knobs 401a and 402a. During inspiratory times valve 401 is open to allow gas flow to port 421, while valve 402 is closed to cut off flow through port 421a. Conversely, valve 402 is open and valve 401 is closed during expiratory times. Port 421a is then open and port 421 is closed.

The valve arrangement 400 can be used with the cylinder 312 shown in FIG. 5 which is identical to the cylinder 312 in FIG. 4, except that port 333 is used as a second inlet port in the FIG. 5 arrangement and a second outlet port 341a is provided in end cap 316 for connection with a second supply line 343a equipped with a one way valve 345a urged toward the closed position by a compression spring 347a. Port 421 is connected with port 331 of the cylinder by a gas line 449 equipped with a check valve 451. Port 421a is similarly connected with port 337 via a line 449a having a check valve 451a.

In operation of the FIG. 5 system, valve 401 makes compressed gas available to chamber 336 through port 421, line 449 and port 331 during inspiratory times. During expiratory times, valve 402 makes gas available to chamber 338 through port 421a, line 449a and port 333 to chamber 338. Thus, when piston 326 is forced to the right during inspiratory times, the gas in chamber 338 is forced through line 343a. Conversely, during expiratory times when the piston is forced to the left, the gas in chamber 336 is delivered to the patient via line 343.

It is thus apparent that each embodiment of the present invention provides a ventilating device which is constructed in a simple and economical manner and which may be easily used, either under neumatic power or manually applied power if a source of pneumatic pressure is unavailable. The device may be quickly and easily assembled and disassembled in the field, and service and maintenance on the device are thus greatly simplified in comparison to more complicated devices.

Decontamination of the device is also easily accomplished. Due to its construction, the ventilating device is light in weight and is thus particularly well suited for use in the field by the armed forces and others who require a portable ventilating device. The device can be stored over extended periods without deterioration of any of its parts, internal or external, and the parts are not subject to undue wear even if the device is used for extended periods of time.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. A gas powered ventilating device for ventilating a patient, said device comprising:
   a substantially enclosed cylinder;
   a piston mounted for reciprocation in said cylinder and dividing the cylinder into a pressure chamber disposed within the cylinder on one side of the piston and a spring chamber disposed within the cylinder on the other side of the piston;
   a ventilation port in said cylinder for receiving ventilating gas to be delivered to the patient;
   a ventilation line extending from said ventilation port for delivering gas therefrom to the patient upon movement of the piston toward the ventilation port to force gas out of the cylinder through said ventilation port and into the ventilation line;
   a compression spring located within said spring chamber inside of the cylinder, said spring acting against the piston to urge same in one direction with increasing force upon progressive compression of the spring; and
   means for supplying gas pressure to said pressure chamber to effect movement of the piston in a direction opposite said one direction until the spring is compressed sufficiently to apply a force to the piston sufficient to move the piston in said one direction, whereby the piston is reciprocated in the cylinder to force gas through said ventilation line during the part of the stroke carrying the piston toward said ventilation port.

2. The device of claim 1, including a handle extending exteriorly of said cylinder and connected with said piston to permit manual operation of the piston in said opposite direction when said gas pressure applying means is disabled.

3. The device of claim 1, wherein said gas pressure applying means comprises:
   a pressure line receiving gas under pressure and applying the gas pressure to said pressure chamber in opposition to the force of said spring; and
   check valve means in said ventilation and pressure lines for allowing flow away from but not toward the pressure chamber in said ventilation line and toward but not away from the pressure chamber in said pressure line.

4. The device of claim 1, wherein:
   said cylinder includes an end plate at one end of said pressure chamber;
   said ventilation port extends through said end plate; and
   said gas pressure applying means comprises a pressure line for applying gas under pressure to said pressure chamber and valve means for regulating flow through said pressure and ventilation lines.

5. The device of claim 4, wherein said valve means comprises:
   a first check valve in said ventilation line allowing flow therein away from but not toward said pressure chamber; and
   a second check valve in said pressure line allowing flow therein toward but not away from said pressure chamber.

6. The device of claim 1, wherein:
   said cylinder includes an end plate at one end of said spring chamber; and
   said ventilation port extends through said end plate.

7. The device of claim 6, including a supply line communicating with a source of the ventilating gas and with said spring chamber to supply the gas thereto upon movement of the piston away from the ventilation port.

8. The device of claim 7, including:
   check valve means for allowing flow in the ventilation line away from but not toward said spring chamber; and
   check valve means for allowing flow in the supply line toward but not away from said spring chamber.

9. The device of claim 1, wherein said ventilation port is disposed in communication with said spring chamber to receive the ventilating gas therefrom, and including a supply line for supplying the ventilating gas to said spring chamber upon movement of the piston away from the ventilation port.

10. The device of claim 9, wherein said gas pressure applying means comprises a pressure line receiving gas under pressure and applying the gas pressure to said pressure chamber.

11. The device of claim 10, including:
   first and second branches of said pressure line extending respectively to said pressure chamber and said spring chamber; and
   valve means for controlling the flow of gas through said first and second branches in a manner to alternately direct gas pressure to said pressure chamber for movement of the piston toward the ventilation port and then to said spring chamber to assist the spring in effecting movement of the piston away from the ventilation port.

12. Apparatus for supplying ventilating gas from a source thereof to a patient, said apparatus comprising:
   an inlet port for connection with the source to receive compressed gas therefrom;
   a first valve connected with said inlet port to received compressed gas therefrom, said first valve opening and closing alternately for preselected times;
   a second valve connected with said first valve to receive compressed gas therefrom when the first valve is open, said second valve opening and closing alternately and being open when the first valve is closed and being closed when the first valve is open; and an outlet port connected with said second valve to receive compressed gas therefrom when the second valve is open, said outlet port being adapted to communicate with the patient to ventilate the patient when the second valve is open and the first valve is closed during inspiratory times that are alternated with expiratory times during which the first valve is open and the second valve is closed to interrupt ventilation of the patient.

13. Apparatus as set forth in claim 12, including flow retsricting means between said inlet port and said first valve.

14. Apparatus as set forth in claim 12, including means for adjusting the durations of the inspiratory and expiratory times.

* * * * *